(12) United States Patent
Allen et al.

(10) Patent No.: US 8,378,167 B2
(45) Date of Patent: Feb. 19, 2013

(54) ARRAY OF WETNESS-SENSING ARTICLES

(75) Inventors: Ansley C. Allen, Neenah, WI (US);
Andrew M. Long, Appleton, WI (US);
Shirlee A. Weber, Neenah, WI (US);
Thomas M. Ales, III, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1347 days.

(21) Appl. No.: 11/414,032

(22) Filed: Apr. 27, 2006

(65) Prior Publication Data

US 2007/0252712 A1 Nov. 1, 2007

(51) Int. Cl.
A61F 13/20 (2006.01)

(52) U.S. Cl. ......... 604/361; 540/573; 540/605; 540/540

(58) Field of Classification Search .................. 604/361; 340/573.5, 605, 540
See application file for complete search history.

(56) References Cited

U.S. PATENT DOCUMENTS

| | | | |
|---|---|---|---|
| 4,100,324 A | 7/1978 | Anderson et al. | |
| 4,704,116 A | 11/1987 | Enloe | |
| 4,798,603 A | 1/1989 | Meyer et al. | |
| 4,940,464 A | 7/1990 | Van Gompel et al. | |
| 5,176,672 A | 1/1993 | Bruemmer et al. | |
| 5,266,928 A * | 11/1993 | Johnson | 340/604 |
| 5,284,703 A | 2/1994 | Everhart et al. | |
| 5,350,624 A | 9/1994 | Georger et al. | |
| 5,486,166 A | 1/1996 | Bishop et al. | |
| 5,490,846 A | 2/1996 | Ellis et al. | |
| 5,509,915 A | 4/1996 | Hanson et al. | |
| 5,570,082 A * | 10/1996 | Mahgerefteh et al. | 340/604 |
| 5,766,389 A | 6/1998 | Brandon et al. | |
| 5,820,973 A | 10/1998 | Dodge et al. | |
| 5,845,644 A | 12/1998 | Hughes et al. | |
| 5,959,535 A * | 9/1999 | Remsburg | 340/604 |
| 5,993,433 A | 11/1999 | St. Louis et al. | |
| 6,248,097 B1 | 6/2001 | Beitz et al. | |
| 6,384,728 B1 * | 5/2002 | Kanor et al. | 340/573.1 |
| 6,417,455 B1 | 7/2002 | Zein et al. | |
| 6,645,190 B1 | 11/2003 | Olson et al. | |
| 6,658,432 B1 | 12/2003 | Alavi et al. | |
| 6,870,479 B2 * | 3/2005 | Gabriel | 340/604 |
| 2002/0145526 A1 | 10/2002 | Friedman et al. | |
| 2007/0049881 A1 | 3/2007 | Ales et al. | |
| 2007/0142797 A1 | 6/2007 | Long et al. | |

FOREIGN PATENT DOCUMENTS

| | | |
|---|---|---|
| EP | 1 398 014 A2 | 3/2004 |
| JP | 2000-175950 A | 6/2000 |
| WO | WO 00/37009 A2 | 6/2000 |

* cited by examiner

Primary Examiner — Tatyana Zalukaeva
Assistant Examiner — Ilya Treyger
(74) Attorney, Agent, or Firm — Randall W. Fieldhack

(57) ABSTRACT

A wetness sensing system includes a first wetness sensing article; a first signaling device producing a first signal upon sensing wetness in the first wetness sensing article, wherein the first signaling device is compatible with the first wetness sensing article; and a second signaling device producing a second signal upon sensing wetness in the first wetness sensing article, wherein the second signaling device is compatible with the first wetness sensing article. Also, a method for enhancing a wetness sensing system includes producing a wetness sensing absorbent article compatible with at least one component of the wetness sensing system, wherein the wetness sensing system includes as components a wetness sensing article and a first signaling device compatible with the wetness sensing article.

33 Claims, 5 Drawing Sheets

ARRAY OF WETNESS-SENSING ARTICLES

BACKGROUND OF THE INVENTION

Absorbent articles such as diapers, training pants, incontinence products, feminine hygiene products, swim undergarments, and the like conventionally include a liquid permeable body-side liner, a liquid impermeable outer cover, and an absorbent core. The absorbent core is typically located in between the outer cover and the liner for taking in and retaining liquids (e.g., urine) exuded by the wearer.

The absorbent core can be made of, for instance, superabsorbent particles. Many absorbent particles, especially super absorbent particles, are so efficient at absorbing liquids that it is sometimes difficult to tell whether or not the absorbent article has been insulted with a body fluid.

Accordingly, various types of moisture or wetness indicators have been suggested for use in wetness sensing absorbent articles. The wetness indicators may include alarm devices that are designed to assist parents or attendants to identify a wet diaper condition quickly upon insult. The devices produce either a visual or an audible signal.

In some embodiments, for instance, inexpensive conductive threads or foils have been placed in the wetness sensing absorbent articles. The conductive materials serve as conductive leads for a signaling device and form an open circuit in the article that can be closed when a body fluid, such as urine, closes the circuit. In these embodiments, although the wetness sensing absorbent articles may be disposable, the signaling devices are not. Thus, the signaling devices are intended to be removed from the article and reattached to a subsequent article.

Problems, however, have been encountered in using such articles for training and/or notification purposes in that a user and/or a caregiver can lose interest in the articles to the point that the efficacy of toilet training and notification are adversely affected. In addition, systems are limited in their flexibility in that they cannot be adapted for different training situations or stages.

SUMMARY OF THE INVENTION

The invention described herein solves these problems and provides an increase in efficacy in using wetness sensing absorbent articles by increasing the interest levels of a user and/or a caregiver and by increasing the level of customizability associated with the wetness sensing absorbent articles. In general, the present disclosure is directed to garments with easy-to-use signaling devices. The signaling device, for instance, may be configured to indicate to a user that a body fluid is present in the wetness sensing absorbent article.

For example, in one embodiment, a wetness sensing system includes a first wetness sensing article; a first signaling device producing a first signal upon sensing wetness in the first wetness sensing article, wherein the first signaling device is compatible with the first wetness sensing article; and a second signaling device producing a second signal upon sensing wetness in the first wetness sensing article, wherein the second signaling device is compatible with the first wetness sensing article.

In another embodiment, a method for enhancing a wetness sensing system includes producing a wetness sensing absorbent article compatible with at least one component of the wetness sensing system, wherein the wetness sensing system includes as components a wetness sensing article and a first signaling device compatible with the wetness sensing article.

In another embodiment, a method for selling wetness sensing articles includes offering for sale a first wetness sensing article in a package including markings to inform a consumer that the package includes a wetness sensing article; and offering for sale a second wetness sensing article in a package including no markings to inform a consumer that the package includes a wetness sensing article.

BRIEF DESCRIPTION OF THE DRAWINGS

The foregoing and other features and aspects of the present invention and the manner of attaining them will become more apparent, and the invention itself will be better understood by reference to the following description, appended claims and accompanying drawings, where:

Figure 1:
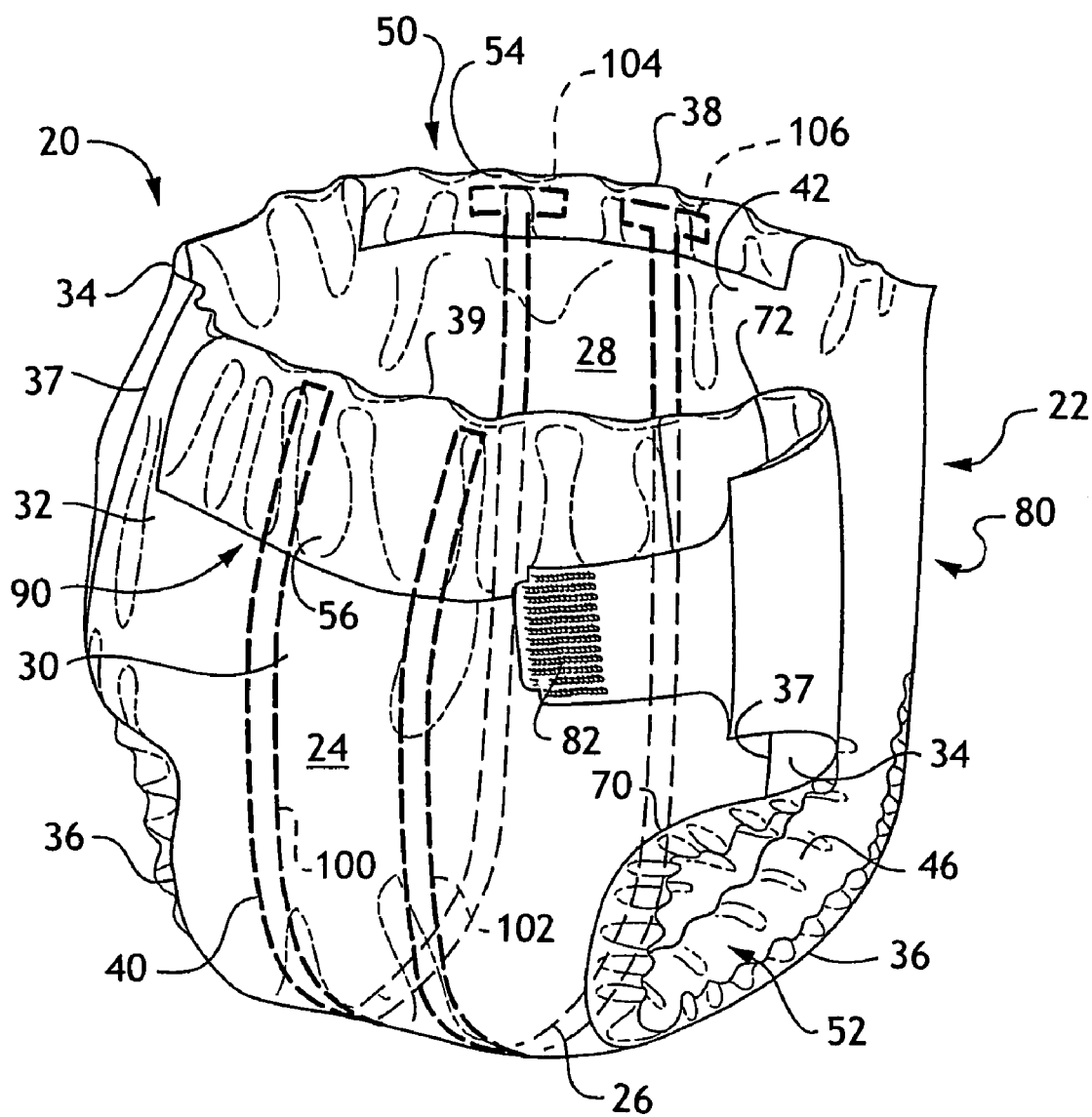
FIG. 1 is a rear perspective view of one embodiment of a wetness sensing absorbent article.

Repeat use of reference characters in the present specification and drawings is intended to represent the same or analogous features or elements of the present invention.

DETAILED DESCRIPTION OF THE INVENTION

It is to be understood by one of ordinary skill in the art that the present discussion is a description of exemplary embodiments only, and is not intended as limiting the broader aspects of the present invention.

The present disclosure is generally directed to wetness sensing absorbent articles adapted to be attached to a signaling device that may be configured to indicate the presence of a body fluid in the absorbent article or other changes in the condition of the product or wearer. The absorbent article may be, for instance, a diaper, a training pant, a pre-fastened pant, a swimming pant, an incontinence product, a feminine hygiene product, a medical garment, a bandage, and the like. Wetness sensing absorbent articles may include an open circuit that becomes closed when a conductive fluid, such as a body fluid, is present in between a pair of conductive leads. Alternatively, wetness sensing absorbent articles may include a closed circuit that becomes open when a fluid, such as a body fluid, is present. In addition, the article may sense wetness based on a change in electrical response to the presence of a bodily fluid where the change in electrical response can be measured as a circuit closing/opening or as a chemical changing characteristics. Generally, the wetness sensing absorbent articles containing the circuit are disposable meaning that they are designed to be discarded after a limited use rather than being laundered or otherwise restored for reuse.

The circuit contained within the wetness sensing absorbent articles of the present disclosure is configured to be attached to a signaling device. The signaling device can provide power to the circuit while also including some type of audible, visible and/or electromagnetic signal that indicates to the user the presence of a body fluid. Although the wetness sensing absorbent article may itself be disposable, the signaling device may be reusable from article to article. In this regard, the present disclosure is particularly directed to different types of attachment mechanisms that allow easy connection between the circuit in the wetness sensing absorbent article and the signaling device. The ease of connection enables the ease of transfer of the signaling device from one wetness sensing absorbent article to another for continuing use.

As described above, the circuit in combination with the signaling device may be configured to indicate the presence of a body fluid contained within the wetness sensing absorbent article. The particular targeted body fluid may vary depending upon the particular type of wetness sensing absorbent article and the desired application. For instance, in one embodiment, the wetness sensing absorbent article comprises a diaper, a training pant, or the like and the signaling device is configured to indicate the presence of urine. Alternatively, the signaling device may be configured to indicate the presence of a metabolite that would indicate the presence of a diaper rash. For adult incontinence products and feminine hygiene products, on the other hand, the signaling device may be configured to indicate the presence of a yeast or of a particular constituent in urine or menses, such as a polysaccharide.

Figure 2:
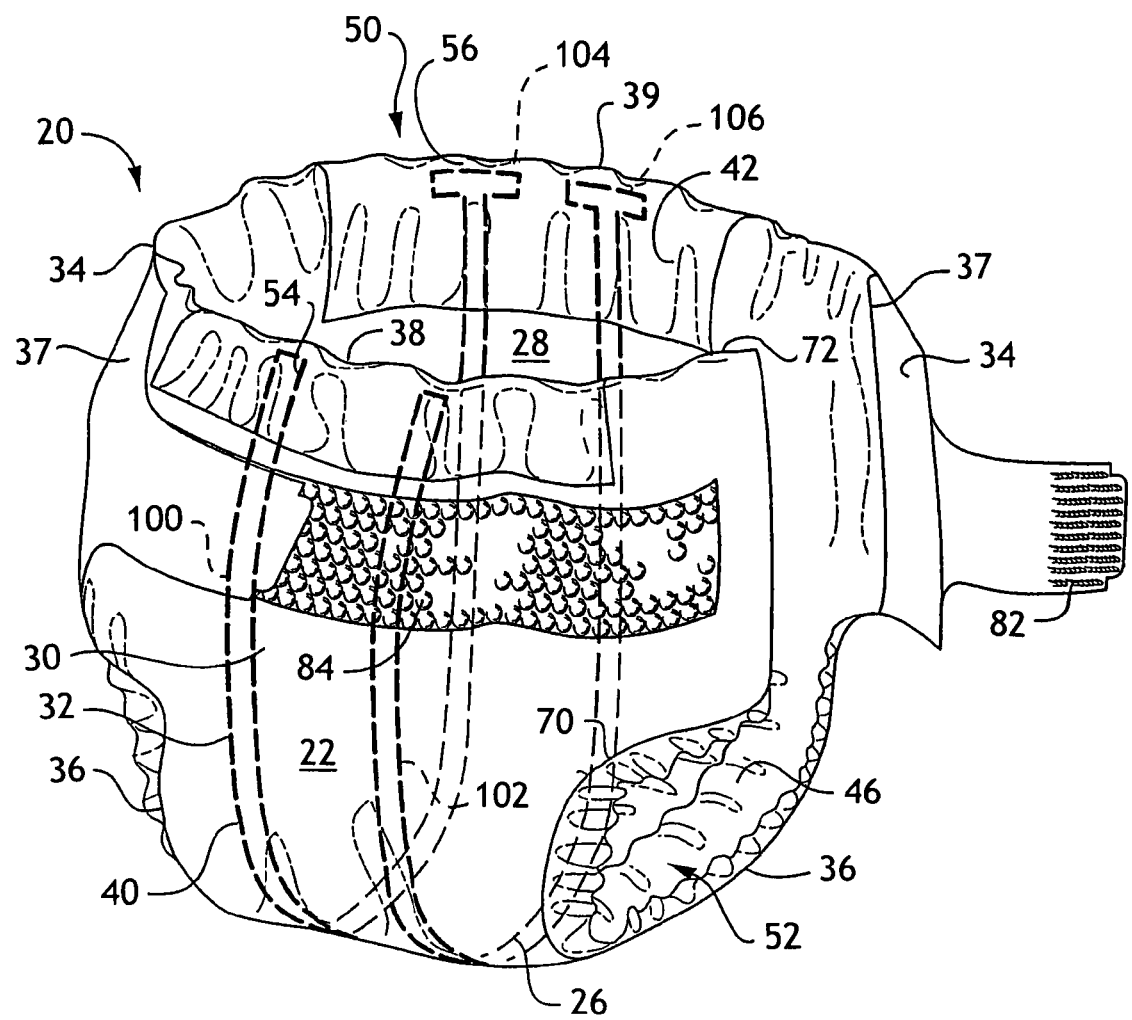
FIG. 2 is a front perspective view of the wetness sensing absorbent article illustrated in FIG. 1.

Referring to FIGS. 1 and 2, for exemplary purposes, a wetness sensing absorbent article 20 is shown. The wetness sensing absorbent article 20 may or may not be disposable. It is understood that the present invention is suitable for use with various other wetness sensing absorbent articles intended for personal wear, including but not limited to diapers, training pants, swim pants, feminine hygiene products, incontinence products, medical garments, surgical pads and bandages, other personal care or health care garments, and the like without departing from the scope of the present invention.

By way of illustration only, various materials and methods for constructing wetness sensing absorbent articles such as the wetness sensing absorbent article 20 of the various aspects of the present invention are disclosed in U.S. Pat. No. 4,798,603 issued Jan. 17, 1989, to Meyer et al.; U.S. Pat. No. 5,176,672 issued Jan. 5, 1993, to Bruemmer et al., U.S. Pat. No. 5,509,915 issued Apr. 23, 1996 to Hanson et al., U.S. Pat. No. 5,993,433 issued Nov. 30, 1999 to St. Louis et al., and U.S. Pat. No. 6,248,097 issued Jun. 19, 2001 to Beitz et al., PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

Figure 3:
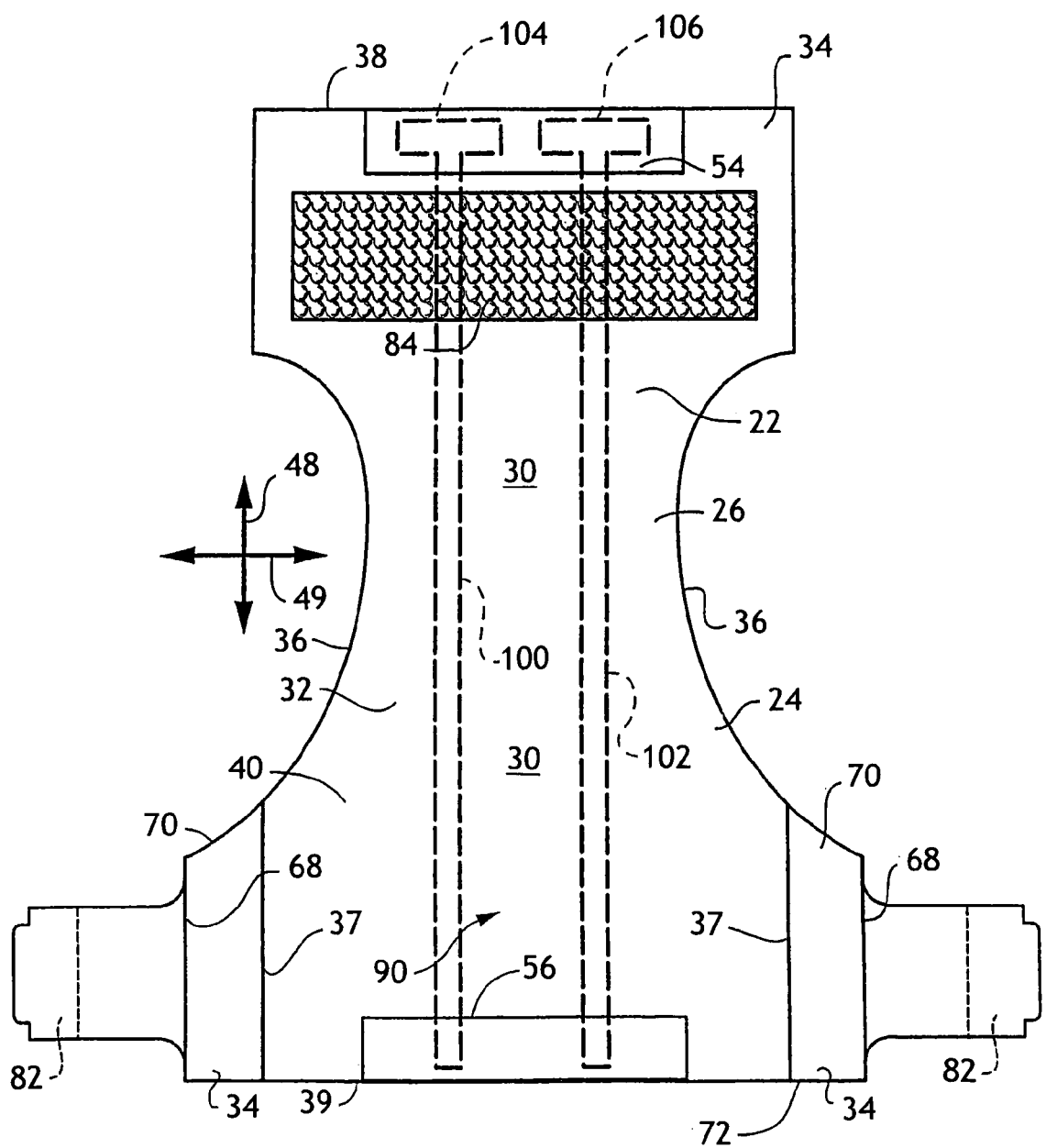
FIG. 3 is a plan view of the wetness sensing absorbent article illustrated in FIG. 1 with the article in an unfastened, unfolded and laid flat condition showing the surface of the article that faces away from the wearer.
Figure 4:
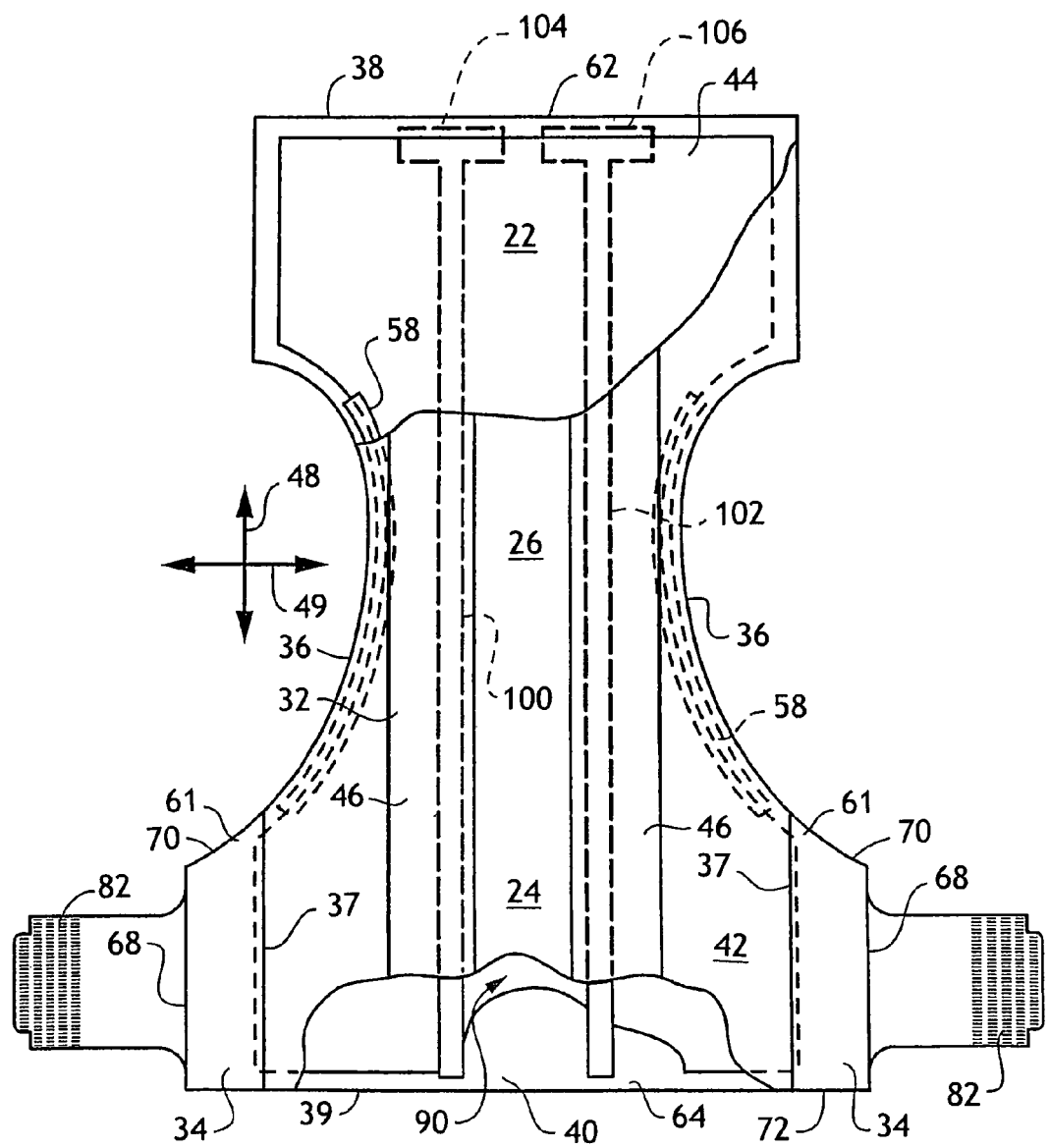
FIG. 4 is a plan view similar to FIG. 3 illustrating the surface of the wetness sensing absorbent article that faces the wearer when worn and with portions cut away to show underlying features.

A wetness sensing absorbent article 20 is representatively illustrated in FIG. 1 in a partially fastened condition. The wetness sensing absorbent article 20 shown in FIGS. 1 and 2 is also represented in FIGS. 3 and 4 in an opened and unfolded state. Specifically, FIG. 3 is a plan view illustrating the exterior side of the wetness sensing absorbent article 20, while FIG. 4 illustrates the interior side of the wetness sensing absorbent article 20. As shown in FIGS. 3 and 4, the wetness sensing absorbent article 20 defines a longitudinal direction 48 that extends from the front of the article when worn to the back of the article. Opposite to the longitudinal direction 48 is a lateral direction 49.

The wetness sensing absorbent article 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The wetness sensing absorbent article 20 also defines an inner surface 28 adapted in use (e.g., positioned relative to the other components of the article 20) to be disposed toward the wearer, and an outer surface 30 opposite the inner surface. The front and back regions 22, 24 are those portions of the wetness sensing absorbent article 20, which when worn, wholly or partially cover or encircle the waist or mid-lower torso of the wearer. The crotch region 26 generally is that portion of the wetness sensing absorbent article 20 which, when worn, is positioned between the legs of the wearer and covers the lower torso and crotch of the wearer. The wetness sensing absorbent article 20 has a pair of laterally opposite side edges 36 and a pair of longitudinally opposite waist edges, respectively designated front waist edge 38 and back waist edge 39.

The illustrated wetness sensing absorbent article 20 includes a chassis 32 that, in this embodiment, encompasses the front region 22, the back region 24, and the crotch region 26. Referring to FIGS. 1-4, the chassis 32 includes an outer cover 40 and a bodyside liner 42 (FIGS. 1 and 4) that may be joined to the outer cover 40 in a superimposed relation therewith by adhesives, ultrasonic bonds, thermal bonds or other conventional techniques. Referring to FIG. 4, the liner 42 may suitably be joined to the outer cover 40 along the perimeter of the chassis 32 to form a front waist seam 62 and a back waist seam 64. As shown in FIG. 4, the liner 42 may suitably be joined to the outer cover 40 to form a pair of side seams 61 in the front region 22 and the back region 24. The liner 42 can be generally adapted, i.e., positioned relative to the other components of the article 20, to be disposed toward the wearer's skin during wear of the wetness sensing absorbent article. The chassis 32 may further include an absorbent structure 44 particularly shown in FIG. 4 disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates.

The elasticized containment flaps 46 as shown in FIG. 4 define a partially unattached edge which assumes an upright configuration in at least the crotch region 26 of the wetness sensing absorbent article 20 to form a seal against the wearer's body. The containment flaps 46 can extend longitudinally along the entire length of the chassis 32 or may extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the wetness sensing absorbent article 20 may also suitably include leg elastic members 58 (FIG. 4), as are known to those skilled in the art. The leg elastic members 58 can be operatively joined to the outer cover 40 and/or the bodyside liner 42 and positioned in the crotch region 26 of the wetness sensing absorbent article 20.

The leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members 58 may include a plurality of dry-spun coalesced multifilament spandex elastomeric threads sold under the trade name LYCRA and available from Invista, Wilmington, Del., U.S.A.

In some embodiments, the wetness sensing absorbent article 20 may further include a surge management layer (not shown) which may be optionally located adjacent the absorbent structure 44 and attached to various components in the article 20 such as the absorbent structure 44 or the bodyside liner 42 by methods known in the art, such as by using an adhesive. A surge management layer helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. Nos. 5,486,166; and 5,490,846. Other suitable surge management materials are described in U.S. Pat. No. 5,820,973. The entire disclosures of these patents are hereby incorporated by reference herein to the extent they are consistent (i.e., not in conflict) herewith.

As shown in FIGS. 1-4, the wetness sensing absorbent article 20 further includes a pair of opposing elastic side panels 34 that are attached to the back region of the chassis 32. As shown particularly in FIGS. 1 and 2, the side panels 34 may be stretched around the waist and/or hips of a wearer in order to secure the garment in place. As shown in FIGS. 3 and 4, the elastic side panels are attached to the chassis along a pair of opposing longitudinal edges 37. The side panels 34 may be attached or bonded to the chassis 32 using any suitable bonding technique. For instance, the side panels 34 may be joined to the chassis by adhesives, ultrasonic bonds, thermal bonds, or other conventional techniques.

In an alternative embodiment, the elastic side panels may also be integrally formed with the chassis 32. For instance, the side panels 34 may comprise an extension of the bodyside liner 42, of the outer cover 40, or of both the bodyside liner 42 and the outer cover 40.

In the embodiments shown in the figures, the side panels 34 are connected to the back region of the wetness sensing absorbent article 20 and extend over the front region of the article when securing the article in place on a user. It should be understood, however, that the side panels 34 may alternatively be connected to the front region of the article 20 and extend over the back region when the article is donned.

With the wetness sensing absorbent article 20 in the fastened position as partially illustrated in FIGS. 1 and 2, the elastic side panels 34 may be connected by a fastening system 80 to define a 3-dimensional wetness sensing absorbent article configuration having a waist opening 50 and a pair of leg openings 52. The waist opening 50 of the article 20 is defined by the waist edges 38 and 39 which encircle the waist of the wearer.

In the embodiments shown in the figures, the side panels are releasably attachable to the front region 22 of the article 20 by the fastening system. It should be understood, however, that in other embodiments the side panels may be permanently joined to the chassis 32 at each end. The side panels may be permanently bonded together, for instance, when forming a training pant or absorbent swimwear.

The elastic side panels 34 each have a longitudinal outer edge 68, a leg end edge 70 disposed toward the longitudinal center of the wetness sensing absorbent article 20, and waist end edges 72 disposed toward a longitudinal end of the wetness sensing absorbent article. The leg end edges 70 of the wetness sensing absorbent article 20 may be suitably curved and/or angled relative to the lateral direction 49 to provide a better fit around the wearer's legs. However, it is understood that only one of the leg end edges 70 may be curved or angled, such as the leg end edge of the back region 24, or alternatively, neither of the leg end edges may be curved or angled, without departing from the scope of the present invention. As shown in FIG. 4, the outer edges 68 are generally parallel to the longitudinal direction 48 while the waist end edges 72 are generally parallel to the transverse axis 49. It should be understood, however, that in other embodiments the outer edges 68 and/or the waist edges 72 may be slanted or curved as desired. Ultimately, the side panels 34 are generally aligned with a waist region 90 of the chassis.

The fastening system 80 may include laterally opposite first fastening components 82 adapted for refastenable engagement to corresponding second fastening components 84. In the embodiment shown in the figures, the first fastening component 82 is located on the elastic side panels 34, while the second fastening component 84 is located on the front region 22 of the chassis 32. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the article 20 in its three-dimensional configuration.

The fastening components 82, 84 may be any refastenable fasteners suitable for wetness sensing absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 include hook fasteners and the second fastening components 84 include complementary loop fasteners. Alternatively, the first fastening components 82 may include loop fasteners and the second fastening components 84 may be complementary hook fasteners. In another aspect, the fastening components 82, 84 can be interlocking similar surface fasteners, or adhesive and cohesive fastening elements such as an adhesive fastener and an adhesive-receptive landing zone or material; or the like. One skilled in the art will recognize that the shape, density and polymer composition of the hooks and loops may be selected to obtain the desired level of engagement between the fastening components 82, 84. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

In the embodiment shown in the figures, the fastening components 82 are attached to the side panels 34 along the edges 68. In this embodiment, the fastening components 82 are not elastic or extendable. In other embodiments, however, the fastening components may be integral with the side panels 34. For example, the fastening components may be directly attached to the side panels 34 on a surface thereof.

In addition to possibly having elastic side panels, the wetness sensing absorbent article 20 may include various waist elastic members for providing elasticity around the waist opening. For example, as shown in the figures, the wetness sensing absorbent article 20 can include a front waist elastic member 54 and/or a back waist elastic member 56.

As described above, the present disclosure is particularly directed to incorporating a body fluid indicating system. One such system is described below. Other systems include a wetness liner such as that described in U.S. Pat. No. 6,658, 432 to Underhill et al., a temperature system, a system in which graphics fade or appear, and any other suitable body fluid indicating system.

One such body fluid indicating system is the wetness indicating system described herein. In this regard, as shown in FIGS. 1-4, the wetness sensing absorbent article 20 includes a first conductive element 100 spaced from a second conductive element 102. In this embodiment, the conductive elements extend from the front region 22 of the wetness sensing absorbent article to the back region 24 without intersecting. The conductive elements 100 and 102 can comprise any suitable conductive material, such as a conductive thread or a conductive foil for example include 112-S silver metallic conductive paste (ink) from Electroscience Laboratories, Inc. and conductive foil described in U.S. Pat. No. 6,417,455 issued Jul. 9, 2002 to Zein et. Al. The first conductive element 100 may not intersect the second conductive element 102 in order to form an open circuit that may be closed, for instance, when a conductive fluid is positioned in between the conductive elements. In other embodiments, however, the first conductive element 100 and the second conductive element 102 may be connected to a sensor within the chassis. The sensor may be used to sense changes in temperature or may be used to sense the presence of a particular substance, such as a metabolite.

In the embodiment shown in FIG. 1, the conductive elements 100 and 102 extend the entire length of the wetness sensing absorbent article 20. It should be understood, however, that in other embodiments the conductive elements may extend only to the crotch region 26 or may extend to any particular place in the wetness sensing absorbent article where a body fluid is intended to be sensed.

The conductive elements 100 and 102 may be incorporated into the chassis 32 at any suitable location as long as the conductive elements are positioned so as to contact a body fluid that is absorbed by the wetness sensing absorbent article 20. In this regard, the conductive elements 100 and 102 generally lie inside the outer cover 40. In fact, in one embodiment, the conductive elements 100 and 102 may be attached or laminated to the inside surface of the outer cover 40 that faces the absorbent structure 44. Alternatively, however, the conductive elements 100 and 102 may be positioned on the absorbent structure 44 or positioned on the liner 42.

The conductive element 100 and 102 may be connected directly to a signaling device, either through direct or indirect contact. The first conductive element 100 may be attached to a first conductive pad member 104, while the second conductive element 102 may be connected to a second conductive pad member 106. The pad members 104 and 106 may be provided for making a reliable connection between the open circuit formed by the conductive elements to a signaling device that is intended to be installed on the chassis by the consumer or manufacturer. The pad members 104 and 106 may create a target zone for attaching the signaling device and the conductive leads or elements. The conductive pad members 104 and 106 may have a relatively large surface area in relation to the conductive elements 100 and 102. For example, the conductive pad members 104 and 106 may have a surface area of at least 1 cm$^2$, at least 2 cm$^2$, and, in one embodiment, at least 3 cm$^2$. For instance, in one embodiment, the surface area of each pad member may be from about 2 cm$^2$ to about 4 cm$^2$.

The position of the conductive pad members 104 and 106 on the wetness sensing absorbent article 20 can vary depending upon where it is desired to mount the signaling device. For instance, in FIGS. 1, 3, and 4, the conductive pad members 104 and 106 are positioned in the front region 22 along the waist opening of the article. In FIG. 2, on the other hand, the conductive pad members 104 and 106 are positioned in the back region 24 along the waist opening of the article. It should be appreciated, however, that in other embodiments, the wetness sensing absorbent article 20 may include conductive pad members being positioned at each end of each conductive element 100 and 102. In still other embodiments, it should be understood that the pad members may be located along the side of the article or towards the crotch region of the article.

The position of the conductive pad members 104 and 106 within the multiple layers of the chassis 32 may also vary depending upon where it is desired to connect the signaling device and the type of attachment mechanism used to make a connection with the signaling device. As described above, the pad members 104 and 106 are electrically connected to the conductive elements 100 and 102. Thus, in one embodiment, the pad members 104 and 106 are positioned below (toward the body side) at least one layer of the outer cover 40. Positioning the pad members 104 and 106 below at least one layer of material may provide various advantages in some embodiments. For instance, locating the pad members 104 and 106 below at least one layer of material within the chassis 32 protects the pad members during shipping and storage and from forming a short circuit during use especially if the pad members are located adjacent one another. Another benefit to placing the pad members under at least one layer of material is the ability to easily manufacture the wetness sensing absorbent article 20 at high machine speeds.

It should be understood, however, that in other embodiments the conductive pad members 104 and 106 may be positioned at an exterior surface of the chassis 32. For instance, the pad members 104 and 106 may be positioned on the outside surface or on the inside surface as desired.

The remaining materials used to form the wetness sensing absorbent article 20 may vary depending upon the particular application and the particular product being produced.

The outer cover 40, for instance, may be breathable and/or may be liquid impermeable. The outer cover 40 may be constructed of a single layer, multiple layers, laminates, spunbond fabrics, films, meltblown fabrics, elastic netting, microporous webs, bonded card webs or foams provided by elastomeric or polymeric materials. The outer cover 40, for instance, can be a single layer of a liquid impermeable material, or alternatively can be a multi-layered laminate structure in which at least one of the layers is liquid impermeable. In other embodiments, however, it should be understood that the outer cover may be liquid permeable. In this embodiment, for instance, the wetness sensing absorbent article may contain an interior liquid barrier layer.

For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Bostik, Inc., of Wauwatosa, Wis., U.S.A., or from National Starch and Chemical Company, Bridgewater, N.J., U.S.A. The liquid permeable outer layer can be any suitable material and is desirably one that provides a generally cloth-like texture. One example of such a material is a 20 gsm (grams per square meter) spunbond polypropylene nonwoven web. The outer layer may also be made of those materials of which the liquid permeable bodyside liner 42 is made.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumburg, Ill., U.S.A.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. A suitable bodyside liner 42 may be manufactured from a wide selection of web materials, such as porous foams, reticulated foams, apertured plastic films, woven and non-woven webs, or a combination of any such materials. For example, the bodyside liner 42 may include a meltblown web, a spunbonded web, or a bonded-carded-web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity.

The absorbent structure 44 may be disposed between the outer cover 40 and the bodyside liner 42. The absorbent structure 44 can be any structure or combination of components which are generally compressible, conformable, non-irritating to a wearer's skin, and capable of absorbing and retaining liquids and certain body wastes. For example, the absorbent structure 44 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular aspect, the absorbent web material is a matrix of cellulosic fluff and superabsorbent hydrogel-forming particles. The cellulosic fluff may include a blend of wood pulp fluff. One preferred type of fluff is identified with the trade designation CR 1654, available from Bowater of Greenville, S.C., USA, and is a bleached, highly absorbent sulfate wood pulp containing primarily southern soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. Methods and apparatus for carrying out such techniques are well known in the art. Furthermore, the absorbent structure may itself encompass multiple layers in the Z direction. Such multiple layers may take advantage of differences in absorbency capacity, such as by placing a lower capacity absorbent material layer closer to the liner 42 and a higher capacity absorbent material closer to the outer cover layer 40. Likewise, discrete portions of an absorbent single-layered structure may encompass higher capacity absorbents, and other discrete portions of the structure may encompass lower capacity absorbents.

As a general rule, the superabsorbent material is present in the absorbent web in an amount of from about 0 to about 90 weight percent based on total weight of the web. The web may have a density within the range of about 0.10 to about 0.60 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and desirably is capable of absorbing more than about 25 times its weight in liquid. Suitable superabsorbent materials are readily available from various suppliers.

For example, SXM 9394, and Favor 9543 superabsorbents are available from DeGussa Superabsorbers.

After being formed or cut into a desired shape, the absorbent web material may be wrapped or encompassed by a suitable tissue or meltblown web or the like wrap sheet that aids in maintaining the integrity and shape of the absorbent structure 44.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference to the extent they are consistent (i.e., not in conflict) herewith.

Figure 5:
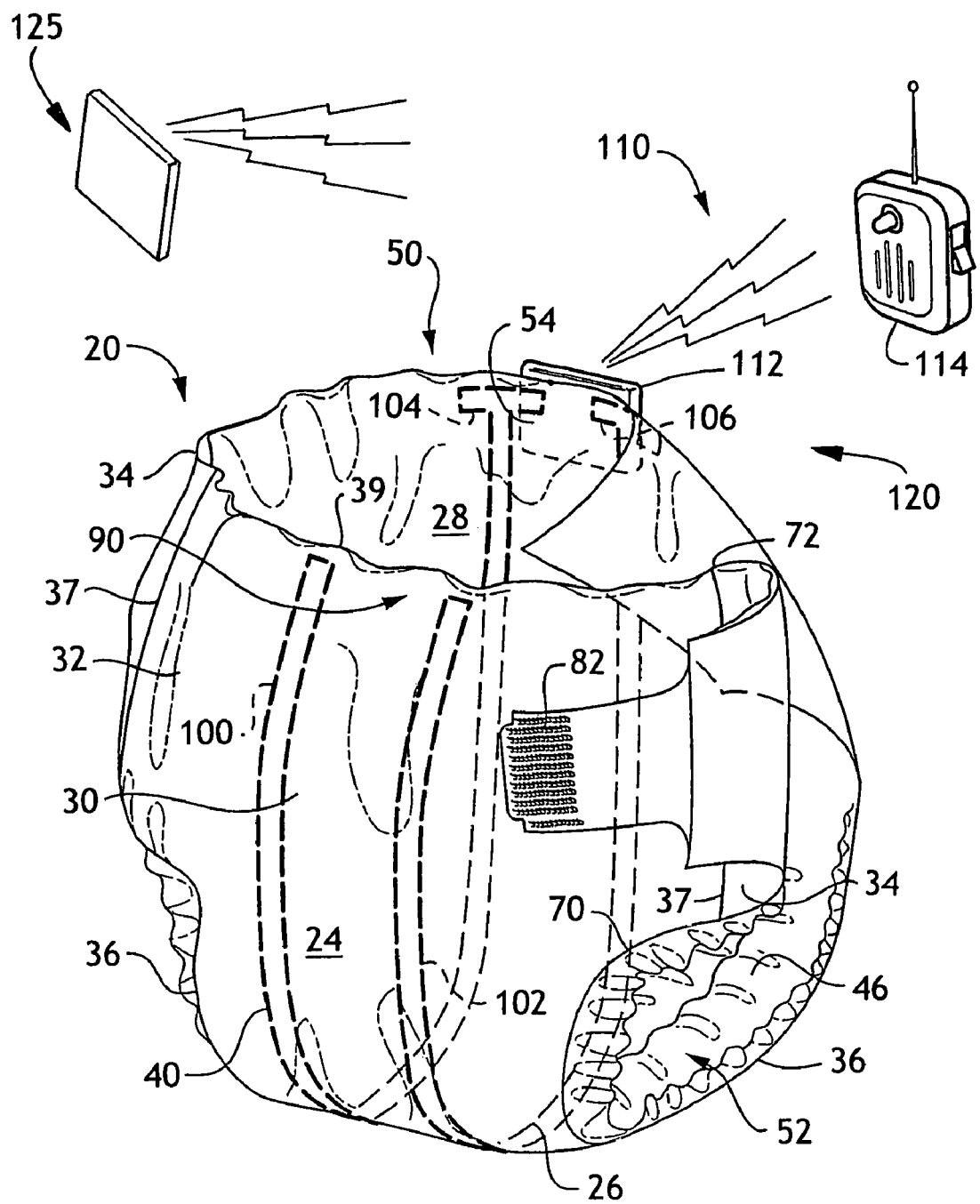
FIG. 5 is a perspective view of the embodiment shown in FIG. 1 further including one embodiment of a wetness sensing system.

Referring to FIG. 5, for exemplary purposes, a signaling device 110 (as depicted by ref. numerals 112 and 114) is shown attached to the conductive pad members 104 and 106. As shown, in this embodiment, the signaling device generally 110 includes a transmitter 112 and a receiver 114. The transmitter 112 includes a pair of opposing terminals that are electrically connected to the corresponding conductive elements. When a body fluid is present in the wetness sensing absorbent article 20, the open circuit formed by the conductive elements 100 and 102 is closed which, in turn, activates the signaling device 110. In particular, in this embodiment, the transmitter 112 sends a wireless signal to the receiver 114 which then indicates to a user that a body fluid is present in the wetness sensing absorbent article 20.

The signaling device 110 can emit an audible signal, a visual signal, or a tactile signal in order to indicate to the user that the circuit has been closed. The audible signal, for instance, may be as simple as one or more beeps to perhaps emitting a musical tune. Similarly, if the signaling device 110 issues a visible signal, the visible signal may comprise a few lights or an interactive display. In still another embodiment, the receiver 114 of the signaling device 110 may be configured to vibrate when the circuit within the wetness sensing absorbent article is closed.

In the embodiment shown in FIG. 5, the signaling device 110 includes a transmitter 112 in combination with a receiver 114. It should also be understood, however, that the signaling device may comprise a single unit that remains attached to the wetness sensing absorbent article 20. For example, the signaling device may be mounted on the wetness sensing absorbent article and issue a visible signal, an audible signal, and/or a tactile signal from the article itself.

In various aspects of the present invention, the absorbent article 20 may include additional features such as those disclosed in co-pending and co-assigned U.S. patent application Ser. No. 11/303,283 to Long, et al. and entitled "Garments With Easy-To-Use Signaling Device"; and U.S. patent application Ser. No. 11/215,937 to Ales, et al. and entitled "Method of Detecting the Presence of an Insult in an Absorbent Article and Device for Detecting the Same"; which are incorporated herein by reference to the extent they are consistent (i.e., not in conflict) herewith. For example, the wetness sensing absorbent article may also include other wetness sensing features such as fading ink, appearing ink, a wetness liner, or a cooling component.

The wetness sensing absorbent article 20 may be a part of a wetness sensing system 120. In one aspect of the present invention, the wetness sensing system 120 includes an wetness sensing absorbent article 20, a first signaling device 110 that is compatible with the wetness sensing absorbent article 20, and a second signaling device 125 that is also compatible with the wetness sensing absorbent article 20. The wetness sensing system 120 may also include a receiver 114. In various aspects of the present invention, the wetness sensing absorbent article 20 may be configured to be used in toilet training a child, in addressing enuresis in a subject, or in monitoring incontinence in a subject, particularly an adult. In one aspect of the present invention, each signaling device manufactured and sold will be compatible with every wetness sensing absorbent article manufactured and sold for any application. For example, a wetness sensing absorbent article 20 may be manufactured and sold for toilet training purposes, and another wetness sensing absorbent article 20 may be manufactured and sold to address enuresis concerns. Likewise, first and second signaling devices 110, 125 may be manufactured and sold that will both be compatible with both the toilet training and enuresis wetness sensing absorbent articles.

In one aspect of the present invention, the wetness sensing system may be enhanced by producing different types of signaling devices beyond the first and second signaling devices 110, 125, or by producing wetness sensing absorbent articles that are also compatible with the first and second signaling devices 110, 125.

In various aspects of the present invention, a first signaling device 110 and a second signaling device 125 may both be manufactured and offered for sale. In one aspect, the first signaling device 110 may produce a first sound, and the second signaling device 125 may produce a second sound, where the first sound is different from the second sound. For example, the first signaling device 110 may produce a popular children's song, while the second signaling device 125 produces a beeping sound. Different sounds may be desired for a number of reasons. For example, in the case of toilet training more than one child, such as with twins or in a child care situation, more than one sound is desirable to differentiate which child is in need of attention. Similarly, in the case of an incontinence monitoring situation, such as in an institutional setting, more than one sound is desirable to differentiate which adult is in need of attention.

In another aspect of the present invention, the first sound may be a positive sound such as a pleasant song, and the second sound may be an unpleasant buzzing sound. A caregiver toilet training a child would select one or the other depending on the progress and goals of the toilet training. The pleasant sound could act as positive reinforcement, and the unpleasant sound could act as negative reinforcement.

In still another aspect of the present invention, the first signaling device 110 may produce a sound, and the second signaling device 125 may produce a wireless signal to transmit to the receiver 114. A caregiver toilet training a child would select one or the other depending on the progress and goals of the toilet training. For example, the caregiver may select a first signaling device 110 that emits a sound for use in toilet training a child in the home, but may choose a second signaling device 125 that emits a wireless signal for use in toilet training the child when in public, to avoid the stigma of a publicly-audible wetness alarm.

In various aspects of the present invention, the second signaling device 125 is a premium signaling device. A premium signaling device offers features beyond those in the more basic signaling devices described above. In one aspect, the premium signaling device produces a plurality of signals. For example, the premium signaling device may produce a plurality of sounds, including, for example, a plurality of songs. In another example, the premium signaling device may produce a plurality of tactile signals. In another example, the premium signaling device may produce a plurality of wireless signals.

In another aspect of the present invention, the premium signaling device may be adapted by any suitable means such that the user may select between the plurality of signals. This is useful, for example, in a situation where a caregiver must differentiate between signals from more than one child or more than one adult as described above. The caregiver can select a different signal for each child or adult. In a further aspect of the present invention, the signal may be switched off, for example, to silence an alarm or to preserve battery life.

In another aspect of the present invention, the plurality of signals in the premium signaling device may include a combination of sounds and wireless signals. This is useful, for example, when the caregiver wants to select a first signal in the form of a sound for use in toilet training a child in the home, but a second signal in the form of a wireless signal for use in toilet training the child when in public, to avoid the stigma of a publicly-audible wetness alarm.

In another aspect of the present invention, the premium signaling device may be adapted by any suitable means to accept sounds or other information downloaded via computer, cell phone, or other device or means. Furthermore, this downloaded information may be downloaded or programmed into the signaling device and be customized to the circumstances of the caregiver and/or subject. This customization may be based on feedback solicited from the caregiver (on frequency of wetting, stage of training, age of the subject, preferences for themes or characters including voices, songs, beeps, etc.) and/or may be based on data on wetting behavior and its progression over time collected within the device.

In one aspect of the present invention in which the second signaling device 125 is a premium signaling device, the first signaling device 110 is suggested to be sold at a first signaling device price, and the second signaling device is suggested to be sold at a second signaling device price. The second signaling device price may be higher than the first signaling device price because of the second signaling device 125 is a premium signaling device. In one aspect of the present invention, a wetness sensing system 120 including a premium signaling device 125 may be sold in association with or near a similar wetness sensing system including a first signaling device 110 in this aspect, the manufacturer and/or retailer may set a price for the wetness sensing system 120 including a premium signaling device higher than the price of a wetness sensing system including a first signaling device 110.

The wetness sensing system 120 described herein allows a manufacturer to produce an wetness sensing absorbent article 20 and first and second signaling devices 110, 125 and package these separately. Each separate package of wetness sensing absorbent article 20, first signaling device 110, and second signaling device 125 may include a description of the condition intended to be addressed by that component of the wetness sensing system 120 (such as the wetness sensing absorbent article 20), a description of the primary function of that signaling device 110, 125, a description of the entire wetness sensing system 120, or some combination thereof. The descriptions may be placed on the packaging, in the packaging, or some combination of both. The descriptions may allow a consumer to become educated as to the conditions that typically dictate the use of a wetness sensing system 120, and the further conditions that may be associated with or experienced in conjunction with the use of a wetness sensing system 120. Such education allow a consumer to make informed decisions as to which signaling device or other associated products to purchase such that the consumer may assemble a customized wetness sensing absorbent article to address various conditions.

Consumer education may be further enhanced by providing indicia on the packaging to indicate various different but associated components of the wetness sensing system 120. The indicia may include graphic design features, text, branding, or any other suitable indicia. For example, all of the packages may exhibit similar graphic design components and branding to identify their association, yet have different coloring and illustrations to identify their differences. These indicia may help a consumer to quickly discern which products may be needed for a particular purpose.

In other words, the wetness sensing system 120 described herein allows a consumer to customize an wetness sensing absorbent article 20 on an as-needed basis to address whatever conditions the wearer may be experiencing without spending more every day for an wetness sensing absorbent article 20 that includes every signaling device and associated product. Consumers desire a high quality, consistent product at a good price with the ability to upgrade for certain circumstances.

The various components of the wetness sensing system 120 may be sold through any retailer, including Internet retailers. Various distributors, wholesalers, hospitals, doctors' offices, and other suitable parties may also be involved. A retailer, for example, locates the various components of the wetness sensing system 120, including packages of the wetness sensing absorbent articles 20, packages of signaling devices 110, 125, and packages of associated products in general proximity to each other on one or more store shelves. Additionally, targeted signaling devices allow for opportunities for advertising systems. For example, a toilet training signaling device could be co-marketed with appropriate rewards or other products associated with toilet training. This proximity allows a consumer to see the components of the wetness sensing system 120 in one place, allows the consumer to read the packaging to learn about the wetness sensing system 120, and allows the consumer to select those components that will address the consumer's needs.

As an example, a consumer wishes to toilet train a child. The consumer also needs an ample supply of pre-fastened pants for everyday use. The consumer, as a part of a typical shopping trip, enters the baby aisle of a store and examines the pants options. The consumer selects a brand of pants, and notices other products located adjacent to and associated with these pants. Upon closer examination, the consumer reads some of the product packaging and learns that a simple first signaling device 110, when added to the pants the consumer is already purchasing, may cut in half the time to toilet train a child. The consumer thus purchases the first signaling device 110 to have on hand for use only during those times when the child is to be toilet trained. The consumer may also purchase a second signaling device 125 to have on hand for toilet training use only during specific training periods. The consumer may also purchase an infant toy and a package of specialty wipes as associated products. The consumer benefits from not needing to pay extra for an everyday pant that contains all of these features. The consumer also benefits because the various signaling devices and associated products are located in one place, rather than being spread across various shelves or an entire store.

For a manufacturer, incorporating some of the improvements into signaling devices and associated products rather than the basic absorbent article allows the manufacturer to make minimal changes to absorbent article machines, resulting in lower capital expenditures and optimizing manufacturing. In addition, researchers may focus on product improvements without considering the effect of the improvements on absorbent article machines. The manufacturer may contract manufacturing of secondary products and enter into joint marketing agreements with makers of related items. Enhancement products may be rapidly introduced and evaluated, and enhancement products need not be as cost sensitive as improvements incorporated into every absorbent article. Finally, customized enhancement products allow the manufacturer to more effectively meet global needs.

From a business standpoint, a wetness sensing system 120 may expand a category because enhancement products may be used with competitors' absorbent articles. Introduction of improvements in signaling devices and associated products may carry a lower risk than incorporating those improvements in an absorbent article.

In various aspects of the present invention, the wetness sensing absorbent article 20 may be disposed in a package. In various aspects, the package may include a rigid material such as cardboard, molded plastic, and the like. In other aspects, the package may be a flexible consumer package. As used herein, the term "flexible consumer package" refers to non-rigid containers, such as polyethylene bags, that are adapted to contain cleansing devices and are adapted to be presented to a consumer.

A wetness sensing absorbent article 20 may be packaged and sold separately from a first signaling device 110 and a second signaling device 125. A wetness sensing absorbent article 20 may be packaged and sold together in the same package with a first signaling device 110. A wetness sensing absorbent article 20 may be packaged and sold together in the same package with a second signaling device 125. A wetness sensing absorbent article 20 may be packaged and sold together in the same package with a first signaling device 110 and a second signaling device 125. A receiver 114 compatible with the first and/or second signaling devices 110, 125 may be packaged with the wetness sensing absorbent articles 20 or may be packaged separately.

In another aspect of the present invention, a consumer may be provided with flexibility in the use of the wetness sensing system 120 by including a plurality of signaling devices in a package with at least one wetness sensing absorbent article 20. In this aspect, the caregiver may select which signaling device to associate with the wetness sensing absorbent article 20 based on the situation in which the wetness sensing absorbent article 20 is to be used. For example, as described above, the caregiver may select a first signaling device 110 that emits a sound for use in toilet training a child in the home, but may choose a second signaling device 125 that emits a wireless signal for use in toilet training the child when in public, to avoid the stigma of a publicly-audible wetness alarm.

In another aspect of the invention, one or more wetness sensing absorbent articles 20 may be packaged and sold with a similar, dissimilar, related, or unrelated product. For example, a wetness sensing absorbent article 20 with a first signaling device 110 may be packaged and sold with a toilet training progress chart.

In another aspect of the present invention, a plurality of signaling devices may be packaged and sold with a single wetness sensing absorbent article 20, or with a plurality of wetness sensing absorbent articles 20. The plurality of signaling devices may be in a 1:1 ratio to the number of wetness sensing absorbent articles 20 in the package, may outnumber the wetness sensing absorbent articles 20 in the package, or may be outnumbered by the wetness sensing absorbent articles 20 in the package.

In another aspect of the present invention, one or more signaling devices may also be packaged separately from a package including one or more wetness sensing absorbent articles 20. The signaling devices may be packaged along a theme, such as a package of age-, gender-, development-stage-, or application-specific signaling devices that may be sold separately from or co-packed with a package of one or more wetness sensing absorbent articles 20.

In another aspect of the present invention, one or more signaling devices that differ from signaling devices that are typically offered may be co-packed with or sold separately from a package of one or more wetness sensing absorbent articles 20. For example, if wetness sensing absorbent articles 20 are typically sold, either packaged together or separately, with signaling devices that play "Twinkle, Twinkle Little Star," a specialty, promotional, or limited-time package of wetness sensing absorbent articles 20 including a signaling device that plays the theme song from a current hit animated movie may be offered. Alternatively, a separate package of the signaling devices that play that theme song without wetness sensing absorbent articles 20 may be offered.

In one aspect of the present invention, wetness sensing absorbent articles 20 of the types described herein may be manufactured. One group of such wetness sensing absorbent articles 20 are packaged and labeled as wetness sensing absorbent articles as part of a wetness sensing system 120 with appropriate labeling, marking, and/or branding to associate that group of wetness sensing absorbent articles 20 with the wetness sensing system 120. Another group of the same wetness sensing absorbent articles 20 may be packaged and labeled as standard or basic absorbent articles without associating them with the wetness sensing system 120. The latter group of wetness sensing absorbent articles 20 would perform similarly to other standard or basic absorbent articles. In this manner, the manufacturer is spared the expense of manufacturing two different lines of essentially identical absorbent articles. Also, a retailer is benefited by needing less stock space and increasing ease of identification. Additionally, the consumer benefits because there is no loss in performance, potentially no cost difference for the enhancements in the article, and flexibility still exists for adding a signaling device after purchase.

In various aspects of the present invention, the wetness sensing system 120 and its components may be branded with the same trademark, with different trademarks from the same trademark owner, or with different trademarks from different trademark owners. For example, a package of wetness sensing absorbent articles 20 including a first signaling device 110 and a separate package with a second signaling device 125 may be sold under the trademark of a known diaper manufacturer. A different signaling device or even a premium signaling device compatible with the wetness sensing absorbent articles 20 may be sold under the trademark of a theme park operator or a movie studio. In this example, the premium signaling devices might only be sold in a theme park run by that theme park operator or at a movie theater showing a movie from that movie studio.

In various aspects, the wetness sensing system 120 may include informational items such as instructions in the use of the product and tips for toilet training, enuresis control, or incontinence control. As used herein, the term "informational item" refers to objects that are provided in addition to wetness sensing absorbent articles, are adapted to communicate information to the user and/or consumer of the wetness sensing absorbent article, and are associated with individual components of the wetness sensing system 120. Examples of informational items include cards, paper, electronic media, printing on the packaging, or other suitable media capable of storing and conveying information.

In various aspects, the informational items associated with the wetness sensing system components may be adapted to appeal to the specific category of user and/or purchaser to which the wetness sensing absorbent article is adapted. The informational items may be adapted, for example, by providing information likely to be of interest to a given category of user and/or purchaser.

For example, a wetness sensing absorbent article may be adapted for use by a caregiver for toilet training purposes. An informational item may be associated with the wetness sensing absorbent article that is adapted to interest caregivers. For example, the informational item may be a card containing information or instructions about children's health and hygiene, such as sleep habits, thumb sucking, teething, skin health, toilet training; questions to ask a child; jokes; and the like, and combinations thereof. The informational item may additionally or alternatively include addresses for web sites available on the Internet. The web sites may contain information related to issues of interest for caregivers and users of wetness sensing absorbent articles.

The informational item may additionally or alternatively include information describing activities that are suitable for caregivers and users of wetness sensing absorbent articles. The activities may be adapted for a child at a specific age, size and/or stage of development. For example, the activities may be adapted to promote interaction between the child and the caregiver.

The informational item may additionally or alternatively include information describing the benefits to be derived from using the wetness sensing system 120. This informational item would be part of a promotional plan emphasizing the customizability of the wetness sensing system 120 for the benefit of the consumer, caregiver, and/or user. This informational item would both explain the use of the various components of the wetness sensing system 120 as well as presenting the additional components that may be available and the various combinations that are possible to achieve different goals.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A wetness sensing system comprising;
a first wetness sensing article;
a first signaling device producing a first signal upon sensing wetness in the first wetness sensing article, wherein the first signaling device is compatible with the first wetness sensing article, and wherein the first signaling device is adapted to be attachable to a wetness sensing article by a consumer; and
a second signaling device producing a second signal upon sensing wetness in the first wetness sensing article, wherein the second signaling device is compatible with the first wetness sensing article, wherein the second signaling device is adapted to be attachable to a wetness sensing article by a consumer, and wherein the second signal is not identical to the first signal.

2. The system of claim 1, wherein the first signal is a first sound, and wherein the second signal is a second sound different from the first sound.

3. The system of claim 2, wherein the first sound is provided for positive reinforcement, and wherein the second sound is provided for negative reinforcement.

4. The system of claim 1, wherein the first signal is a sound signal, a visual signal, or a tactile signal, and wherein the second signal is a wireless transmission to a receiver.

5. The system of claim 1, wherein the first wetness sensing article and the first signaling device are disposed in a package.

6. The system of claim 5, wherein the second signaling device is disposed in the package.

7. The system of claim 1, wherein the second signaling device is a promotional item available for only a limited time.

8. The system of claim 1, wherein the first wetness sensing article and the first signaling device are branded with the same trademark.

9. The system of claim 1, wherein the first wetness sensing article is branded with a trademark from one trademark owner, and wherein the first signaling device is branded with a trademark from a different trademark owner.

10. The system of claim 1, wherein the second signaling device is a premium signaling device.

11. The system of claim 10, wherein the premium signaling device produces a plurality of signals.

12. The system of claim 11, wherein the premium signaling device is adapted such that a use may select from the plurality of signals.

13. The system of claim 11, wherein the plurality of signals is a plurality of sound signals, visual signals, or tactile signals.

14. The system of claim 11, wherein the plurality of signals is a plurality of wireless signals.

15. The system of claim 11, wherein the plurality of signals includes a sound and a wireless signal.

16. The system of claim 11, wherein one of the plurality of signals can be switched off.

17. The system of claim 10, wherein the premium signaling device is adapted to receive downloaded signals.

18. The system of claim 1, wherein the first wetness sensing article is adapted to be used for toilet training.

19. The system of claim 1, further comprising a second wetness sensing article different from the first wetness sensing article, wherein the first signaling device is compatible with both the first and second wetness sensing articles.

20. The system of claim 19, wherein both of the first and second wetness sensing articles are compatible with each of the first and second signaling devices.

21. The system of claim 19, wherein the second wetness sensing article is adapted to be used to prevent enuresis.

22. The system of claim 19, wherein the first and second wetness sensing articles are branded with the same trademark.

23. The system of claim 19, wherein the first wetness sensing article is branded with a trademark from one trademark owner, and wherein the second wetness sensing article is branded with a trademark from a different trademark owner.

24. The system of claim 19, further comprising a third wetness sensing article different from the first and second wetness sensing articles, wherein the first signaling device is compatible with the first, second, and third wetness sensing articles.

25. The system of claim 24, wherein the third wetness sensing article is adapted to be used to monitor incontinence.

26. The system of claim 1, further comprising a receiver compatible with the first signaling device.

27. The system of claim 26, wherein the first wetness sensing article, the first signaling device, and the receiver are packaged together in one package.

28. The system of claim 1, wherein the wetness sensing article further includes fading ink, appearing ink, a wetness liner, or a cooling indicator.

29. The system of claim 1, further comprising instructions for a caregiver in the use of the wetness sensing article to toilet train a subject.

30. The system of claim 1, wherein the wetness sensing article is diaper, a pre-fastened pant, or a swimming pant.

31. The system of claim 1, wherein the wetness sensing article is an adult incontinence product.

32. The system of claim 1, further comprising a promotional plan focusing on the benefits to be derived from using the wetness sensing system.

33. The system of claim 32, wherein the promotional plan includes customizability of the wetness sensing system.

* * * * *